United States Patent
Tran et al.

(10) Patent No.: US 6,562,070 B2
(45) Date of Patent: *May 13, 2003

(54) ANTERIOR CHAMBER PHAKIC LENS

(75) Inventors: Son Trung Tran, Arlington, TX (US);
Stephen J. Van Noy, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/044,763

(22) Filed: Jan. 9, 2002

(65) Prior Publication Data

US 2003/0018385 A1 Jan. 23, 2003

Related U.S. Application Data

(63) Continuation of application No. 09/908,378, filed on Jul. 18, 2001, now Pat. No. 6,395,028.

(51) Int. Cl.[7] .................................................. A61F 2/16
(52) U.S. Cl. ..................................... 623/6.44; 623/6.47
(58) Field of Search .............................. 623/6.38, 6.39, 623/6.41, 6.42–6.55

(56) References Cited

U.S. PATENT DOCUMENTS

| | | | |
|---|---|---|---|
| 4,149,279 A | 4/1979 | Poler | |
| 5,071,432 A | 12/1991 | Baikoff et al. | |
| 5,192,319 A * | 3/1993 | Worst | 623/6.43 |
| 5,300,117 A | 4/1994 | Baikoff | |
| 5,928,282 A | 7/1999 | Nigam | |
| 6,083,231 A | 7/2000 | Van Noy et al. | |
| 6,129,760 A | 10/2000 | Fedorov et al. | |
| 6,143,001 A | 11/2000 | Brown et al. | |
| 6,152,959 A | 11/2000 | Portney | |
| 6,171,337 B1 | 1/2001 | Galin | |
| 6,190,410 B1 | 2/2001 | Lamielle et al. | |
| 6,197,059 B1 | 3/2001 | Cumming | |
| 6,342,058 B1 | 1/2002 | Portney | |
| 6,395,028 B1 * | 5/2002 | Tran et al. | 623/6.44 |
| 6,409,763 B1 | 6/2002 | Brady | |

FOREIGN PATENT DOCUMENTS

| | | |
|---|---|---|
| WO | WO 98/56315 | 12/1998 |
| WO | WO 01/87182 A2 | 11/2001 |
| WO | WO 01/87188 A2 | 11/2001 |

* cited by examiner

Primary Examiner—Corrine McDermott
Assistant Examiner—Hieu Phan
(74) Attorney, Agent, or Firm—Jeffrey S. Schira

(57) ABSTRACT

An anterior chamber phakic lens made from an elastomeric, foldable, highly biocompatible material. The lens has a generally circular optic and integrally formed plate-style haptics, the haptics containing an opening into which project a pair of pincer arms. the pincer arms are sized and shaped so as to pull away from each other when the lens is folded, and are draw back toward each other when the folded lens is released and allowed to return to its unfolded state. Such movement allows the pincers to gather a small section of the iris so as to hold the lens in place.

4 Claims, 2 Drawing Sheets

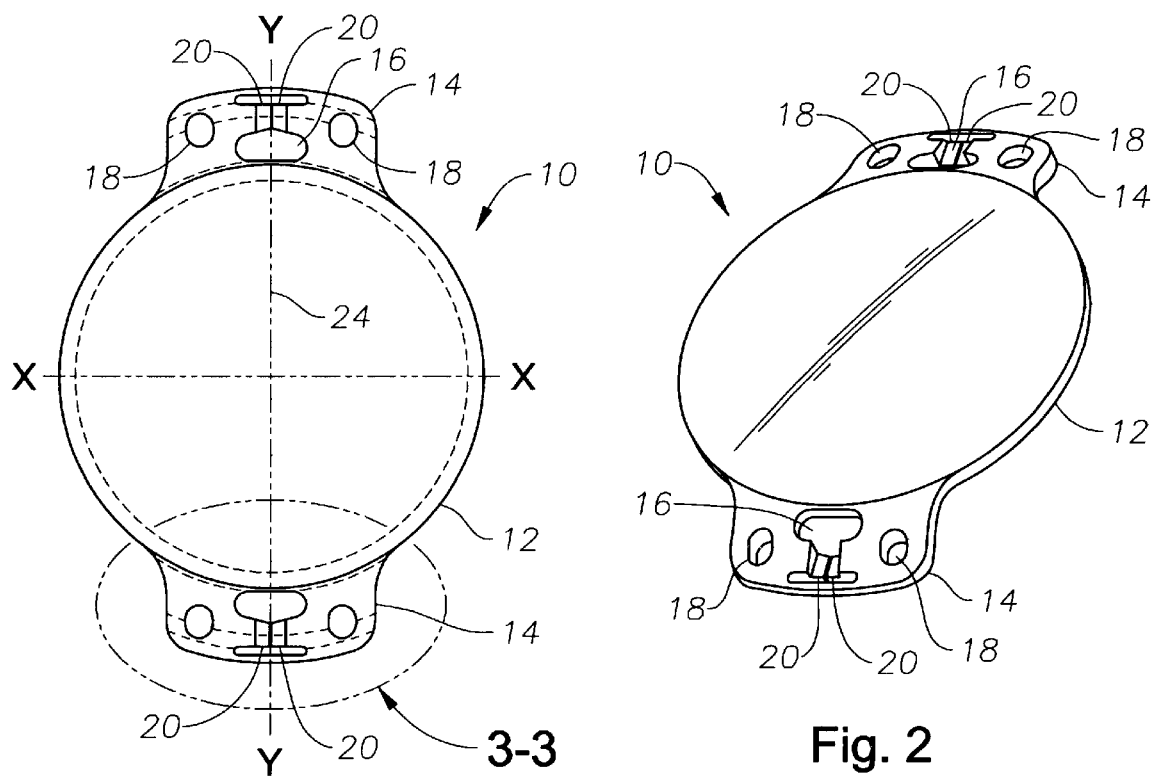
Fig. 1
Fig. 2
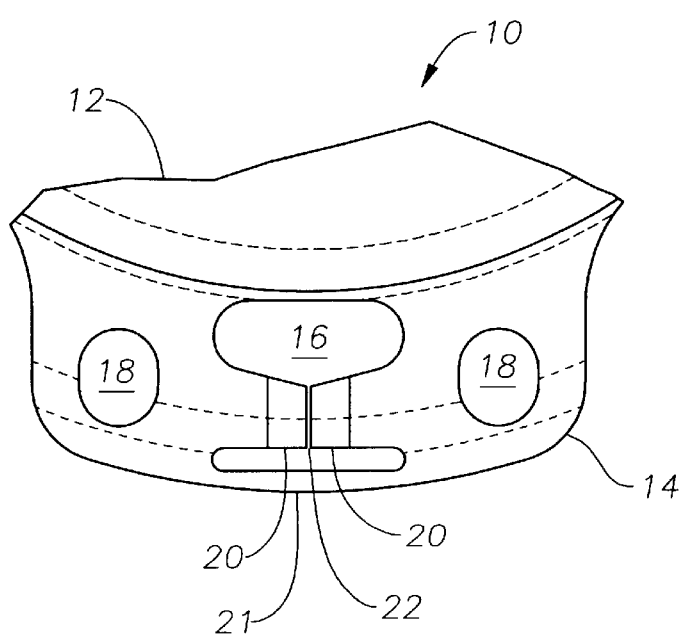
Fig. 3

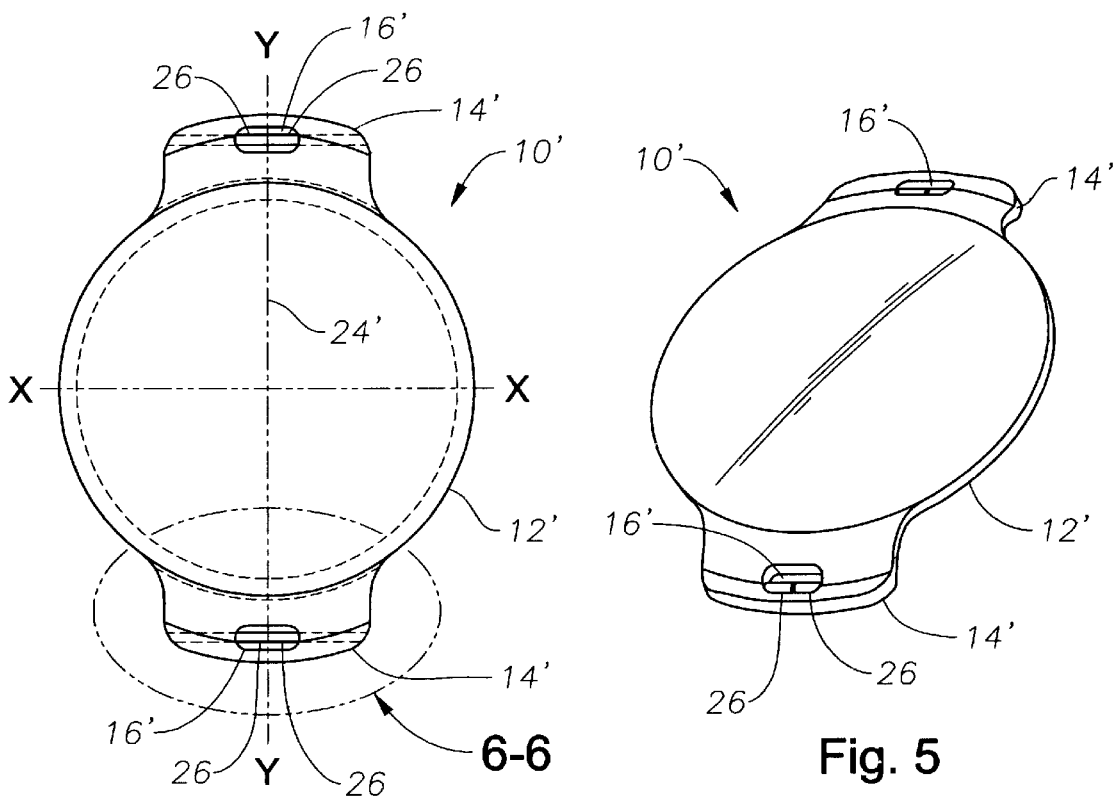
Fig. 4
Fig. 5
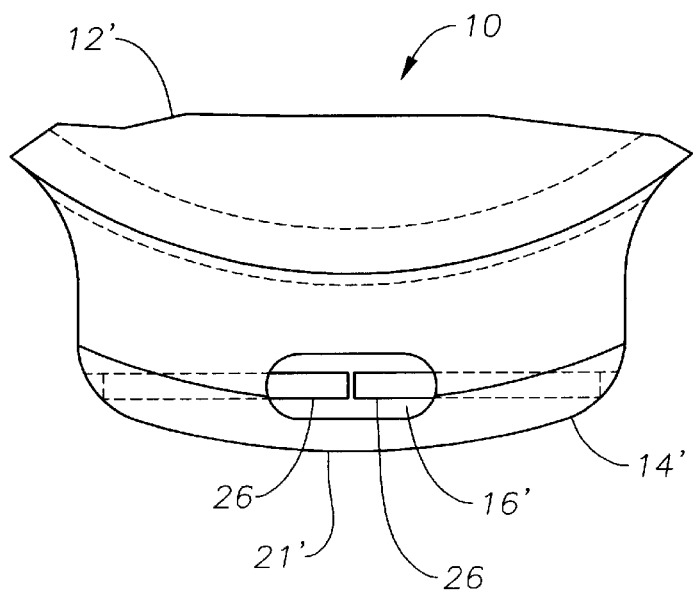
Fig. 6

ANTERIOR CHAMBER PHAKIC LENS

This application is a continuation of U.S. application Ser. No. 09/908,378, filed Jul. 18, 2001, now U.S. Pat. No. 6,395,028.

BACKGROUND OF THE INVENTION

This invention relates generally to the field of intraocular lenses (IOL) and, more particularly, to anterior chamber phakic IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea also may be asymmetric or toric, resulting in an uncompensated cylindrical refractive error referred to as corneal astigmatism. In addition, due to age-related reduction in lens accommodation, the eye may become presbyopic resulting in the need for a bifocal or multifocal correction device.

In the past, axial myopia, axial hyperopia and corneal astigmatism generally have been corrected by spectacles or contact lenses, but there are several refractive surgical procedures that have been investigated and used since 1949. Barraquer investigated a procedure called keratomileusis that reshaped the cornea using a microkeratome and a cryolathe. This procedure was never widely accepted by surgeons. Another procedure that has gained widespread acceptance is radial and/or transverse incisional keratotomy (RK or AK, respectively). Recently, the use of photablative lasers to reshape the surface of the cornea (photorefractive keratectomy or PRK) or for mid-stromal photoablation (Laser-Assisted In Situ Keratomileusis or LASIK) have been approved by regulatory authorities in the U.S. and other countries. All of these refractive surgical procedures cause an irreversible modification to the shape of the cornea in order to effect refractive changes, and if the correct refraction is not achieved by the first procedure, a second procedure or enhancement must be performed. Additionally, the long-term stability of the correction is somewhat variable because of the variability of the biological wound healing response between patients.

Several companies are investigating implantable anterior chamber phakic IOLs, including Bausch & Lomb's NuVita and Model ZB5M lenses, and the Artisian iris claw lens by Ophtec BV. These and other anterior chamber phakic lenses are described in U.S. Pat. Nos. 5,071,432 (Baikoff), 5,192,319 (Worst), 5,300,117 (Baikoff, et al.), 5,928,282 (Nigam) and PCT Publication No. WO 98/56315. The clinic experience with commercially available anterior chamber phakic lenses has not been entirely satisfactory does to difficult implantation techniques and clinical complications such as endothelial cell loss and pupil ovaling.

Prior art iris-fixated anterior chamber lenses, such as those described in U.S. Pat. No. 6,152,959 (Portney) and U.S. Pat. No. 5,192,319 (Worst) which is commercially available as the Artisan lens from Ophtec BV are made from polymethyl methacrylate (PMMA), which is a relatively hard thermoplastic and not considered to be a foldable material. The hardness of the iris fixating pincers arms makes it difficult to gather enough iris tissue within the pincer arms to hold the lens because the surgeon must pull the relatively rigid arms apart while simultaneously gather iris tissue into the gap between the arms. In addition, the rigidity of PMMA requires that the gap between the pincer arms in the relaxed state be relatively large so as to avoid injuring the iris. See, for example at column 2, lines 66–67 of Portney '959 where the preferred pincer gap is described as being between 0.05 mm and 0.25 mm. Such a large gap requires that a great deal of iris tissue be gather within the gap in order to hold the lens stable on the iris.

Therefore, a need continues to exist for a safe, biocompatible and easily fixated anterior chamber phakic intraocular lens.

BRIEF SUMMARY OF THE INVENTION

The present invention improves upon the prior art by providing an anterior chamber phakic lens made from an elastomeric, foldable, highly biocompatible material. The lens has a generally circular optic and integrally formed plate-style haptics, the haptics containing an opening into which project a pair of pincer arms. the pincer arms are sized and shaped so as to pull away from each other when the lens is folded, and are draw back toward each other when the folded lens is released and allowed to return to its unfolded state. Such movement allows the pincers to gather a small section of the iris so as to hold the lens in place.

Accordingly, one objective of the present invention is to provide a safe and biocompatible intraocular lens.

Another objective of the present invention is to provide a safe and biocompatible intraocular lens that is easily fixated on the iris.

Still another objective of the present invention is to provide a safe and biocompatible intraocular lens that is stable in the anterior chamber.

These and other advantages and objectives of the present invention will become apparent from the detailed description and claims that follow.

BRIEF DESCRIPTION OF THE DRAWING

FIG. 1 is a top plan view of a first embodiment of the lens of the present invention.

FIG. 2 is a perspective view of a first embodiment of the lens of the present invention.

FIG. 3 is an exploded plan view of a haptic of a first embodiment of the lens of the present invention taken at circle 3—3 in FIG. 1.

FIG. 4 is a top plan view of a second embodiment of the lens of the present invention.

FIG. 5 is a perspective view of a second embodiment of the lens of the present invention.

FIG. 6 is an exploded plan view of a haptic of a second embodiment of the lens of the present invention taken at circle 6—6 in FIG. 4.

DETAILED DESCRIPTION OF THE INVENTION

As best seen in FIGS. 1, 2, 4 and 5, lens 10 and 10' of the present invention generally include optic 12 and 12' and at least two plate-style haptic 14 and 14' integrally formed with optic 12 and 12', respectively. Optics 12 and 12' may be of any suitable size, such as between 4.5 mm and 6.5 mm in diameter, and may be biconcave, biconvex, concave/convex or any other suitable geometry. Optics 12 and 12' may also contain refractive or diffractive features, such features being well-known in the art. Lens 10 and 10' are preferably formed in any suitable overall diameter from a soft, foldable material such as a hydrogel, silicone or soft acrylic, such diameters and materials being well-known in the art. As best seen in FIGS. 3 and 6, haptics 14 and 14' contain a central opening 16 and 16', respectively and as seen in FIGS. 1–3, may also contain positioning or manipulation holes 18. Holes 18 also help reduce the overall weight of lens 10. the outer periphery of haptics 14 and 14' contain outer stiffening bands 21 and 21', respectively, that help to stiffen haptics 14 and 14'. Although FIGS. 1–6 illustrate opening 16 and 16' as being oval and oriented in the X—X direction, one skilled in the art will recognize that opening 16-16' may be round, oval or any other suitable shape and oriented in any suitable direction, including along the Y—Y direction.

As best seen in FIGS. 1–3, projecting into opening 16 and integrally formed with haptics 14 are a plurality of pincer arms 20. Pincer arms 20 are thinner than haptics 14, as best seen in FIG. 2, and contain gap 22 that is less than 0.05 mm, preferably between 0.01 mm and 0.03 mm, and most preferably 0.02 mm, although some touching of pincer arms 20 may occur.

In use, lens 10 is folded anteriorly along 12-6 axis 24, which bisects haptics 14. Folding lens 10 along axis 24 causes pincer arms 20 to pivot, pull apart and project posteriorly from optic 12. When lens 10 is placed on the iris of an eye in the folded condition and released, lens 10 gradually returns to its natural, unfolded state, so that pincer arms 20 return to their nearly touching position shown in FIG. 3. The return pivoting movement of pincer arms 20 while lens 10 is sitting on the iris causes pincer arms 20 to gather iris tissue within gap 22, so that little or no manipulation of pincer arms 20 is required by the surgeon to fixate lens 10 on the iris. Alternatively, pincer arms 20 may be pulled apart, iris tissue pulled up into gap 22 and pincer arms 20 released so that pincer arms 20 trap iris tissue within gap 22. Lens 10 may also be injected into an eye using any suitable injection cartridge, such as the cartridge disclosed in U.S. Pat. Nos. 6,083,231 and 6,143,001, the entire contents of which being incorporated herein by reference.

Alternatively, as seen in FIGS. 4–6, pincer arms 26 may be formed separately of haptics 14' from well-known filamentous materials such as polypropylene or PMMA and attached to haptics 14' in a manner well-known in the art. Lens 10' may be implanted in the manner described above.

This description is given for purposes of illustration and explanation. It will be apparent to those skilled in the relevant art that changes and modifications may be made to the invention described above without departing from its scope or spirit.

We claim:

1. An intraocular lens, comprising:
   a) an optic;
   b) at least two plate-style haptics, the haptics containing an opening; and
   c) a pair of opposing pincer arms connected to the haptics and projecting into the opening, the pincer arms being thinner than the haptics.

2. The lens of claim 1 wherein the pincer arms are integrally formed with the haptics.

3. An intraocular lens, comprising:
   a) an optic;
   b) at least two plate-style haptics, the haptics containing an opening; and
   c) a pair of opposing pincer arms connected to the haptics and projecting into the opening so as to bisect the opening.

4. The lens of claim 3 wherein the pincer arms are integrally formed with the haptics.

* * * * *